(12) United States Patent
Toriya et al.

(10) Patent No.: US 7,582,057 B2
(45) Date of Patent: Sep. 1, 2009

(54) ENDOSCOPIC SYSTEM USING AN EXTREMELY FINE COMPOSITE OPTICAL FIBER

(75) Inventors: Tomoaki Toriya, Sakura (JP); Takashi Tsumanuma, Sakura (JP); Kenichi Nakatate, Sakura (JP); Takashi Ishii, Sakura (JP); Kiyoshi Oka, Ibaraki-ken (JP); Toshio Osaki, Yokohama (JP); Akiyoshi Hayakawa, Inuyama (JP)

(73) Assignees: Japan Atomic Energy Research Institute, Kashiwa (JP); Fujikura Ltd., Tokyo (JP); Kawasaki Jukogyo Kabushiki Kaisha, Kobe (JP)

(*) Notice: Subject to any disclaimer, the term of this patent is extended or adjusted under 35 U.S.C. 154(b) by 320 days.

(21) Appl. No.: 11/061,722

(22) Filed: Feb. 22, 2005

(65) Prior Publication Data

US 2005/0192480 A1 Sep. 1, 2005

(30) Foreign Application Priority Data

Feb. 24, 2004 (JP) ............................. 2004-047579
Aug. 23, 2004 (JP) ............................. 2004-242099

(51) Int. Cl.
*A61B 1/06* (2006.01)
*A61B 1/04* (2006.01)

(52) U.S. Cl. ........................................ 600/160; 600/108

(58) Field of Classification Search ................ 600/108, 600/109, 160, 182, 175–178; 385/142, 144
See application file for complete search history.

(56) References Cited

U.S. PATENT DOCUMENTS 4,604,992 A * 8/1986 Sato ........................... 600/108
4,648,892 A * 3/1987 Kittrell et al. ................. 65/387
4,664,474 A * 5/1987 Tanaka et al. ................ 385/127
4,759,604 A 7/1988 Utsumi et al.
4,807,597 A * 2/1989 Tsuno et al. ................. 600/177
4,834,070 A * 5/1989 Saitou ......................... 600/108
4,896,941 A * 1/1990 Hayashi et al. ............. 385/116
4,975,102 A * 12/1990 Edahiro et al. ................ 65/391

(Continued)

FOREIGN PATENT DOCUMENTS

JP 08-240728 3/1995

(Continued)

OTHER PUBLICATIONS

Kenichi, Nakatate, JP-08-240728-Quartz-Based Image Fiber for Near Infrared Ray and Extremely Fine Diameter Endoscope Using the Same, Published: Sep. 17, 1996, JPO, Abstract (English Translation of Abstract p. 1 of 1).*

*Primary Examiner*—Linda C Dvorak
*Assistant Examiner*—Alireza Nia

(57) ABSTRACT

Endoscopic system 40 comprises composite optical fiber 34 that consists of a large-diameter, laser light transmitting optical fiber surrounded by a large number of image transmitting fibers that are bundled together to form an integral assembly with the central fiber, laser applying and image observing optical unit 42 that is connected to the eyepiece portion of said composite optical fiber such that it launches laser light into said large-diameter optical fiber and that the image being transmitted through said image transmitting optical fiber is focused on a camera to become observable, and an illuminating light transmitting unit that transmits illuminating light to the tip of the objective portion of said composite optical fiber for irradiation purposes.

17 Claims, 3 Drawing Sheets

U.S. PATENT DOCUMENTS

| | | | |
|---|---|---|---|
| 5,048,923 A * | 9/1991 | Tsumanuma et al. | 385/117 |
| 5,116,317 A | 5/1992 | Carson, Jr. et al. | |
| 5,243,612 A * | 9/1993 | Udagawa et al. | 372/22 |
| 5,293,872 A * | 3/1994 | Alfano et al. | 600/475 |
| 5,608,835 A * | 3/1997 | Ono et al. | 385/126 |
| 6,944,494 B2 * | 9/2005 | Forrester et al. | 600/478 |
| 2002/0156380 A1 * | 10/2002 | Feld et al. | 600/473 |
| 2002/0196337 A1 * | 12/2002 | Takeyama | 348/131 |
| 2005/0219552 A1 * | 10/2005 | Ackerman et al. | 356/603 |

FOREIGN PATENT DOCUMENTS

| | | |
|---|---|---|
| JP | 07-222712 | 8/1995 |
| JP | 08114717 | 7/1996 |
| JP | 10170839 | 6/1998 |
| JP | 2003001465 | 1/2003 |

* cited by examiner

ENDOSCOPIC SYSTEM USING AN EXTREMELY FINE COMPOSITE OPTICAL FIBER

BACKGROUND OF THE INVENTION

This invention relates to an endoscopic apparatus primarily intended for medical use. More particularly, the invention relates to an endoscopic apparatus using an extremely fine composite optical fiber as an integral assembly of an image transmitting optical fiber for use in the finding and diagnosis of a lesion and a large-diameter, laser transmitting optical fiber for use in the treatment of the lesion.

Heretofore, endoscopes using a fused monolithic image fiber or an optical fiber such as an image bundle have been commercialized in various types. Transmitting laser light to the lesion over the optical fiber is also a commercialized technique in laser therapy.

Conventionally, the endoscope and the laser transmitting optical fiber are physically independent of each other and must be inserted into the human body either through separate holes or via the lumens of catheter tubes.

In a non-medical field and for the purpose of cutting and welding metals, laser machining methods and systems have been proposed and they employ a composite optical fiber that consists of a large-diameter, machining laser light transmitting fiber surrounded by a large number of image transmitting fibers that are bundled together to form an integral assembly with the central fiber (see, for example, JP 9-216086A, JP 9-216087A and JP 2003-1465A).

The laser machining method or system proposed by JP 2003-1465A is shown in FIG. 5; a YAG laser oscillator emits a machining laser beam which passes through an optical fiber to be guided to a laser combining dichroic beam splitter, from which the combined laser beam is reflected to get into incident optics, where it is processed to become passable through a composite optical fiber; thereafter, the laser beam travels through the composite optical fiber to be introduced into an output section, where it is focused to irradiate the work.

Illuminating laser light, on the other hand, passes through an illuminating light guiding optical fiber to be guided into the dichroic beam splitter, where it is added to the center of the machining laser; the combined laser beam enters the incident optics, where it is processed to become passable through the composite optical fiber; thereafter, the illuminating laser beam travels through the composite optical fiber to be introduced into the output section, where it is focused with the machining laser beam to irradiate the work.

The image carrying laser beam is reflected from the work and travels in opposite direction to pass through the output section, the composite optical fiber, incident optics, beam splitter and finally through an interference filter to reach a monitor unit which displays the image of the illuminated lesion.

In all conventional laser therapeutic systems, the endoscope which is responsible for image observation is physically independent of the laser light transmitting optical fiber, so the image of the lesion needs to be checked either through the endoscope or by external x-ray monitoring. With the laser light transmitting optical fiber inserted into the human body until it comes close enough to the lesion, the doctor performs treatment by applying laser light to the lesion while checking the position of the optical fiber with the aid of the image obtained from the endoscope or by x-ray monitoring.

This technique requires that the surgeon perform laser application by first making visual check of the lesion and the optical fiber either through the endoscope or by x-ray monitoring and then, on the basis of the obtained image information, exercising his or her discretion in directing the tip of the optical fiber to the desired position with respect to the lesion.

However, directing the tip of the laser illuminating optical fiber to the desired position with respect to the lesion largely depends on the skill and discretion of the operator and so does the accuracy with which the applied laser light can fall on the target position of the lesion. What is more, unwanted exposure to x-rays from the outside can cause not only a safety problem but also inconsistency in the efficacy of laser therapy.

The conventional composite optical fibers described in JP 9-216086A, JP 9-216087A and JP 2003-1465A which have a laser light transmitting section and an image transmitting section are all intended to be used under exposure to radiation or to transmit laser light of high output power. Since those composite optical fibers are fabricated from a stepped-index fiber whose core is made of pure quartz glass, it has been difficult to reduce the fiber diameter small enough to be suitable for use on endoscopes.

SUMMARY OF THE INVENTION

The present invention has been accomplished under those circumstances and has as an object providing an endoscopic system whose diameter is small enough to allow for easy observation of the interior of the human body and which enables simultaneous observation of image with treatment by laser light irradiation.

To attain the stated object, the present invention provides an endoscopic system comprising a composite optical fiber that consists of a large-diameter, laser light transmitting optical fiber surrounded by a large number of image transmitting fibers that are bundled together to form an integral assembly with the central fiber, a laser applying and image observing optical unit that is connected to the eyepiece portion of said composite optical fiber such that it launches laser light into said large-diameter optical fiber and that the image being transmitted through said image transmitting optical fiber is focused on a camera to become observable, and an illuminating light transmitting unit that transmits illuminating light to the tip of the objective portion of said composite optical fiber for irradiation purposes.

In the endoscopic system of the present invention, said large-diameter optical fiber and said image transmitting optical fiber are each preferably an optical fiber which has $GeO_2$ doped quartz glass as the core and of which the core/cladding index difference $\Delta$ is 2-5%.

In another preferred embodiment, said illuminating light transmitting unit comprises a light source and a light guide that transmits the illuminating light emerging from said light source, at least the tip portion of said light guide being made integral with said image transmitting fiber in its longitudinal direction.

In yet another preferred embodiment, the endoscopic system of the present invention further includes a video monitor for displaying an image signal as it is picked up from said laser applying and image observing optical unit.

Said laser applying and image observing optical unit preferably includes a beam splitter that reflects the emission of laser light from a laser oscillator to be launched into said large-diameter optical fiber and which transmits the image traveling through said image transmitting optical fiber so that it is focused on said camera.

The endoscopic system of the present invention has the advantage that by simply inserting a single fiberscope into the human body, the image of the lesion can be observed simultaneously with its treatment by laser light irradiation such that the surgeon can accurately apply the laser light to the lesion while examining a clear picture of the latter. As a matter of course, there is no need to fear for the risk of exposure to x-rays through external irradiation.

In addition, erroneous irradiation can be prevented since continuous image observation is possible not only during the application of laser light but also after that as well.

As a further advantage, the lesion can be irradiated with the required intensity of laser light for the required time duration while checking them visually and, hence, superior therapeutic effect and high safety can be obtained.

DETAILED DESCRIPTION OF THE INVENTION

This invention relates to an endoscopic apparatus primarily intended for medical use, which is characterized by using a composite optical fiber as an integral assembly of an image transmitting image fiber for use in the finding and diagnosis of a lesion and a large-diameter, laser transmitting optical fiber for use in the treatment of the lesion and which has a sufficiently small diameter to allow for easy insertion into the human body.

The conventional composite optical fibers described in JP 9-216086A, JP 9-216087A and JP 2003-1465A which have a laser light transmitting section and an image transmitting section are all intended to be used under exposure to radiation or to transmit laser light of high output power and they have been fabricated from a stepped-index fiber whose core is made of pure quartz glass having superior radiation resisting characteristics. The composite optical fiber to be used in the present invention is characterized in that the large-diameter, laser light transmitting optical fiber and the image transmitting optical fiber are each preferably an optical fiber whose core is made of $GeO_2$ doped quartz glass and which has a core/cladding index difference $\Delta$ in the range of 2-5%. Using these design parameters, the present inventors could successfully reduce the diameter of the composite optical fiber to a comparable level to the image fiber employed in medical fiberscopes.

A version of the image transmitting optical fiber employed in the conventional composite optical fiber has a diameter of 1.7 mm with 15,000 pixels. When in an uncoated state, this optical fiber serving as the pixel basis has a core/cladding index difference $\Delta$ of about 1% and a pixel-to-pixel spacing of about 10 μm has been necessary to perform appropriate image transmission. Hence, if one uses this conventional image transmitting optical fiber to form an image transmitting section having a large number of pixels, the diameter of the composite optical fiber increases so much as to introduce difficulty in adopting it in an endoscopic fiberscope which in practical use is inserted into the human body. On the other hand, the image transmitting optical fiber to be used in the endoscopic system of the present invention has its core/cladding index difference $\Delta$ adjusted to lie within the range of 2-5%, preferably 3.5-4%, with the result that the core-to-core spacing can be reduced to as small as 3 μm; given the same number of pixels, the diameter of the image transmitting optical fiber can be reduced to 0.3 times the conventional value.

Figure 1:
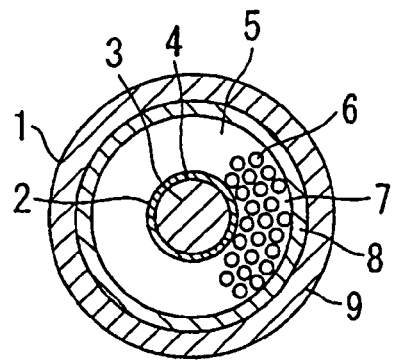
FIG. 1 is a cross-sectional view showing an example of the composite optical fiber for use in the endoscopic system of the present invention.

FIG. 1 is a cross-sectional view showing an example of the composite optical fiber that can advantageously be used in the present invention and which is generally indicated by numeral 1. Indicated by numeral 2 is a large-diameter fiber that is primarily intended for laser transmission and which consists of a core 3 made of $GeO_2$ doped quartz glass and a cladding 4 made of pure quartz glass. The diameter of the core 3 is preferably in the range of 50-400 μm whereas the diameter of the cladding 4 preferably ranges from about 1.02 to about 1.3 times the core diameter, with the numerical aperture (NA) of the large-diameter fiber 2 typically ranging from about 0.2 to about 0.4.

If the diameter of the core 3 is less than 50 μm, the power of the laser light that can be transmitted is restricted, decreasing the likelihood to offer adequate efficacy in laser therapy. If the diameter of the core 3 is greater than 400 μm, it becomes difficult to achieve the desired reduction in the diameter of the composite optical fiber 1.

If the numerical aperture of the large-diameter fiber 2 is within the range of 0.2 to 0.4, it can be materialized using quartz-based optical fibers and appropriate values can be chosen in accordance with a specific object of laser light irradiation, such as applying laser light with a maximum divergence of angle or irradiating a narrow area. It should be mentioned that there is no need to have a numerical aperture match between the large-diameter fiber 2 and the image transmitting optical fiber 5 to be described just below.

The large-diameter fiber 2 is surrounded by a large number of image transmitting fibers 5 that are bundled together. The image transmitting fibers 5 are fused to form a monolithic sea-island structure in which a large number of cores 6 as islands are surrounded by a continuous phase of cladding 7 like a sea. The cores 6 are made of $GeO_2$ doped quartz glass and the cladding 7 is made of either pure quartz glass or fluorine or otherwise doped quartz glass. Adjacent cores 6 are spaced apart by a distance of about 3 μm. The number of the image transmitting fibers 5 in a bundle represents the number of pixels and it preferably ranges from about 1,000 to 100,000.

As already mentioned, the spacing between cores 6 is set from the value of the core/cladding index difference $\Delta$ and by adjusting the value of $\Delta$ to lie between 2 and 5%, preferably between 3.5 and 4%, the core-to-core spacing can be reduced to as small as 3 μm. If the number of pixels as defined above is less than 1,000, there is high likelihood for the failure to obtain a sharp image; if the number of pixels exceeds 100,000, it becomes difficult to manufacture a composite optical fiber of the desired small diameter.

As another embodiment of a composite optical fiber which can be used in this invention, a core 3 of the large-diameter optical fiber 2 is made of pure quartz glass or a $GeO_2$ doped quartz glass, a cladding 4 of the large-diameter optical fiber is made of a fluorine or otherwise doped quartz glass having a lower reflective index than the core, a core 6 of the image transmitting optical fiber 5 is made of a $GeO_2$ doped quartz glass, and a cladding 7 of the image transmitting optical fiber is made of pure quartz glass or a fluorine or otherwise doped quartz glass having a lower reflective index than the pure quartz glass.

The image transmitting optical fiber can be used for transmitting infrared radiation in addition to image observation using visible light.

To make the composite optical fiber 1 in the embodiment under consideration, a rod of large-diameter fiber 2 is placed at the center of a quartz tube serving as a quartz jacket layer 8 and then surrounded by optical fibers serving as image transmitting fibers 5 which are packed together to form a perform, which is then drawn down to a smaller-diameter fiber. In this drawing step, the quartz jacket layer 8 is preferably covered with a silicone resin, UV curable resin, polyimide resin, etc. to form a resin coating layer 9 in a thickness of from about 20 to about 100 µm. By adjusting the thickness of the resin coating layer 9 to be within the stated range, a composite optical fiber having the intended small diameter can be fabricated and yet it meets the requirement for guaranteed strength.

The outside diameter of the jacket layer on the composite optical fiber 1 of the above-described structure can preferably be adjusted to range from about 0.3 mm to about 2 mm depending on the number of pixels to be presented.

If the core-to-core spacing is written as d and the circle diameter as D, the number of pixels N is determined by the following equation:

$$N = 0.9 \times (D/d)^2 \quad (1)$$

After determining d from the index difference Δ and given the required number of pixels N, the circle diameter D is calculated from Eq. (1). The outside diameter of the jacket layer is about 1.1 times the circle diameter.

Figure 2:
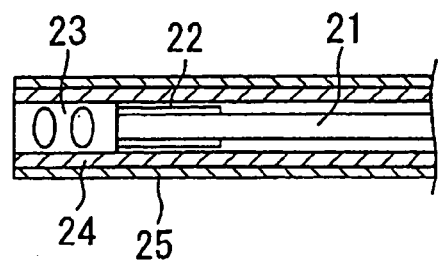
FIG. 2 is a longitudinal section of an example of the objective portion of a fiberscope which is to be used in the endoscopic system of the present invention.

FIG. 2 shows an exemplary structure of the objective portion of a fiberscope employing the composite optical fiber. To the tip of the composite optical fiber 21, a sleeve 22 is bonded and after polishing its surface, the tip is fitted with an objective lens unit 23. The objective lens unit 23 is handled as the objective portion of an image fiber used in an ordinary fiberscope and it is surrounded by a lightguide fiber 24 over which illuminating light is transmitted to irradiate the area of interest, thereby forming the objective portion of a fiberscope. The lightguide fiber 24 preferably uses a multi-component glass optical fiber, which may optionally be replaced by a quartz fiber or a plastic clad fiber.

The multi-component glass optical fiber is available in very small fiber diameters ranging from 30 to 50 µm. In the case of fine fiberscopes, the illuminating fiber has to be inserted into a very small space, so the use of a particularly small-diameter fiber is preferred. The angle of viewing of fiberscopes is generally wide (60°-120°) and the multi-component glass optical fiber is suitable for the purpose of illuminating such a wide range of area. With the quartz-based optical fiber, the minimum fiber diameter and the angle of illumination that can be obtained are about 70 µm and 30 degrees, respectively, making it difficult for a fiberscope of high finder coverage to illuminate the entire area under observation.

The entire objective portion is inserted into a protective tube 25 and bonded to its inner surfaces to form the tip at the objective end of the fiberscope. The protective tube 25 may be a resin tube such as a fluoroplastic (e.g. PTFE, EFFE or PFA) tube, polyurethane tube or polyimide tube; alternatively, it may be a metal pipe such as a stainless steel pipe.

Figure 3:
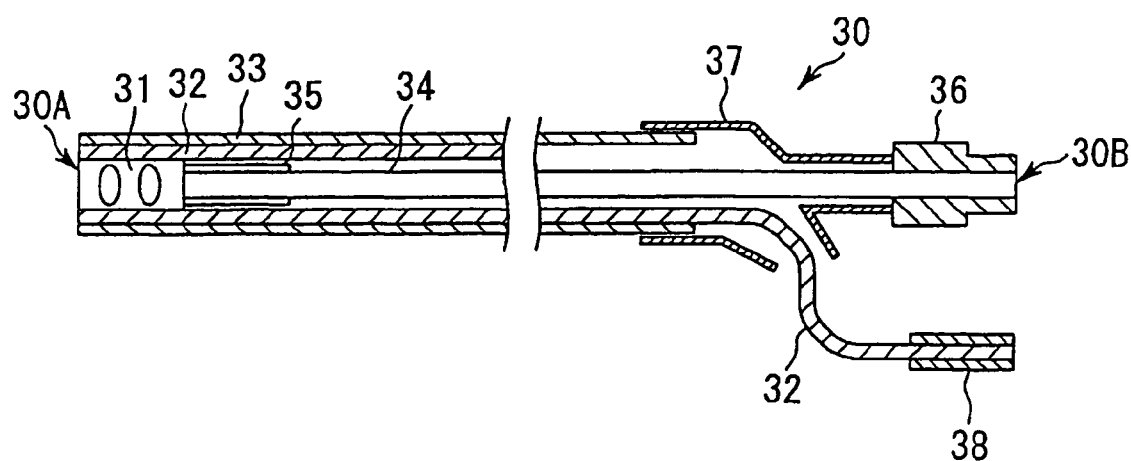
FIG. 3 is a longitudinal section of an example of the fiberscope which is to be used in the endoscopic system of the present invention.

FIG. 3 shows an exemplary fiberscope using the composite optical fiber as it is generally indicated by 30. The principal components of the fiberscope 30 are: the composite optical fiber 34; an objective lens unit 31 provided at the objective end 30A of the fiberscope; a terminal connector 36 provided at the eyepiece end 30B; a lightguide fiber 32 provided along the composite optical fiber 34; a protective tube 33 enclosing the above-mentioned components; and a branch 37 provided at the eyepiece end of the protective tube 33 to receive the lightguide fiber 32.

The objective end 30A of the fiberscope 30 is composed by inserting the objective lens unit 31 and the lightguide fiber 32 into the protective tube 33 and bonding them in position. A sleeve 35 is bonded to the objective end of the composite optical fiber 34 and its end face is polished. A terminal connector 36 is bonded to the eyepiece end 30B of the fiberscope 30, with its fiber end being polished. The lightguide fiber 32 diverges at the branch 37 and fitted with a terminator 38 for establishing connection to an illuminating device.

Figure 4:
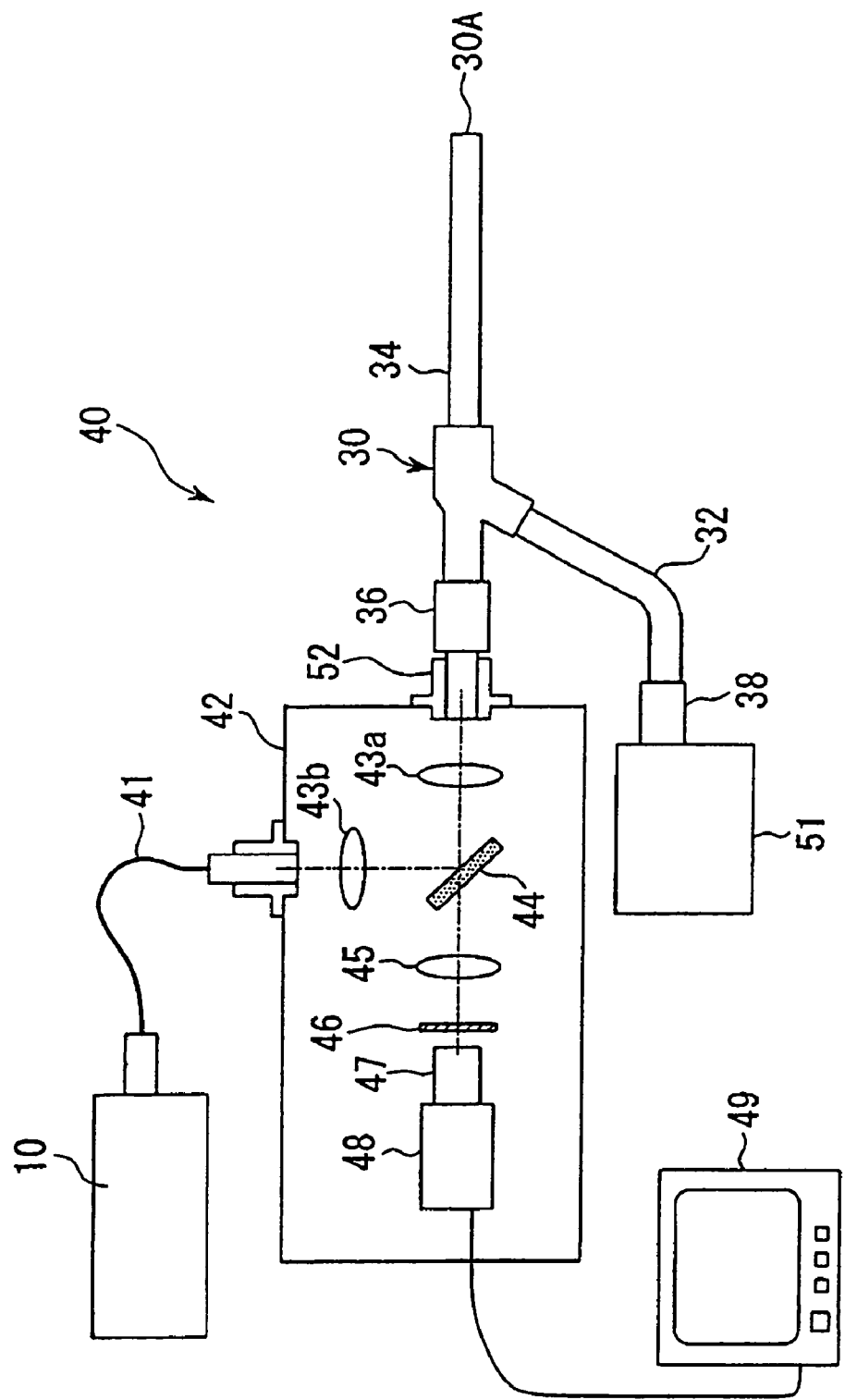
FIG. 4 shows diagrammatically an example of the endoscopic system of the present invention.
Figure 5:
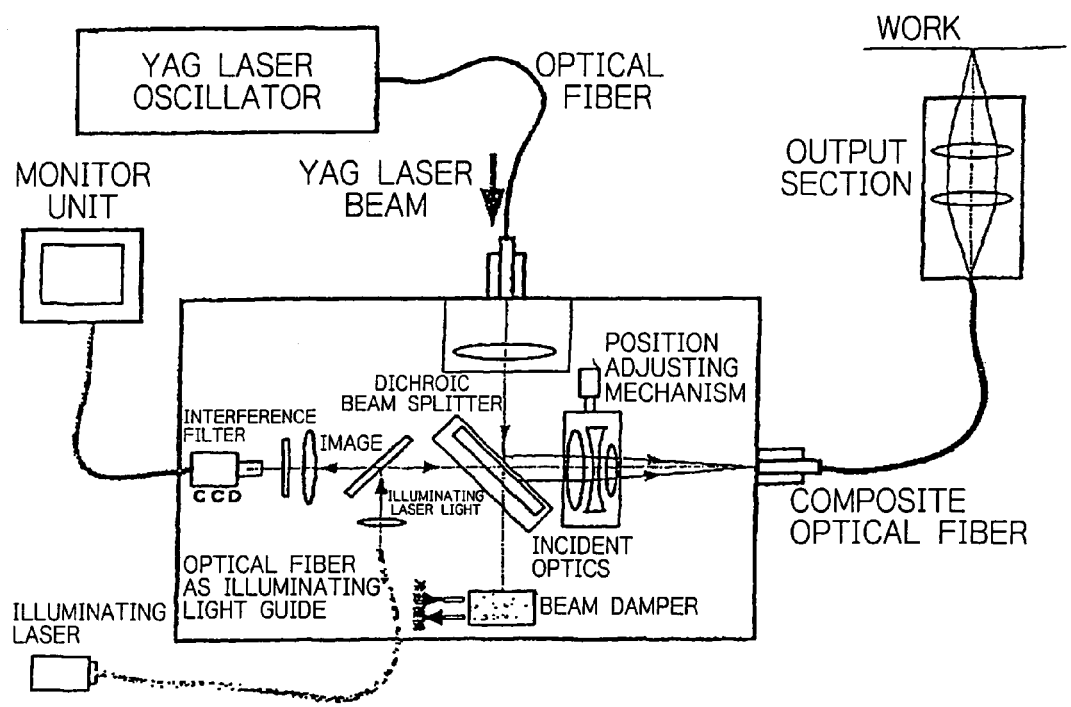
FIG. 5 shows an exemplary laser machining system which employs the conventional composite optical fiber.

FIG. 4 shows an example of an endoscopic observation system according to the present invention which is generally indicated by 40. The endoscopic observation system 40 comprises: the fiberscope 30 having the composite optical fiber 34 and the lightguide fiber 32; a laser applying and image observing optical assembly 42 connected to the eyepiece portion of the fiberscope 30; a laser oscillator 10 that transmits laser to the laser applying and image observing optical assembly 42 via an optical fiber 41; an illuminator 51 that illuminates the objective end of the fiberscope 30 with light as it is passed through the lightguide fiber 32; and a video monitor 49 which displays an image signal as it is picked up from the laser applying and image observing optical assembly 42. The laser applying and image observing optical assembly 42 is so adapted that laser light is launched into the large-diameter optical fiber in the composite optical fiber 34 whereas the image carrying laser light traveling in opposite direction through the image transmitting optical fiber forms a focused image on a CCD camera 48 such that it is observable by the operator.

The terminal connector 36 at the eyepiece end of the fiberscope 30 is fitted on an adapter 52 of the laser applying and image observing optical assembly 42. The lightguide fiber 32 is connected at the terminator 38 to the illuminator 51. The optical fiber 41 connecting the laser oscillator 10 to the laser applying and image observing optical assembly 42 may be of the same type as the large-diameter optical fiber in the composite optical fiber 34 but this is not the sole case of the present invention. If the laser oscillator 10 is small in size, it may be directly connected to the laser applying and image observing optical assembly 42; alternatively, a mirror, lenses and other optional optics may be combined for transmitting laser light.

The laser applying and image observing optical assembly 42 comprises: the CCD camera 48 fitted with a camera lens 47; a beam splitter 44 which reflects the laser light from the laser oscillator 10 to be launched into the large-diameter fiber and which also transmits the image carrying laser light traveling in opposite direction through the image transmitting optical fiber to form a focused image on the CCD camera 48; an optical unit composed of condenser lenses 43a and 43b and a relay lens subunit 45; and an interference filter 46 for blocking the laser light.

The image carrying laser light traveling through the image transmitting optical fiber in the composite optical fiber 34 passes through the condenser lens 43a, the visible light transmitting beam splitter 44, the relay lens subunit 45 and the laser light blocking interference filter 46; it then passes through the camera lens 47 to form a focused image on the CCD camera 48. An image signal outputted from the CCD camera 48 is displayed on the video monitor 49. The operator can manipulate the fiberscope 30 while observing the image being displayed on the video monitor 49.

Laser light emitted from the laser oscillator 10 travels through the optical fiber 41 to be transmitted to the laser applying and image observing optical assembly 42, from which it passes through the condenser lens 43b, is reflected by the beam splitter 44 and then passes through the condenser lens 43a to be launched into the core of the large-diameter optical fiber in the composite optical fiber 34; the laser light emerges from the objective end 30A of the fiberscope 30 to irradiate the area under observation.

The laser oscillator 10 can choose the most suitable laser light depending on the severity of the lesion and the regimen of treatment. For example, a variety of lasers having wavelengths ranging from the visible to the near infrared region may be employed and they include a dye laser, an argon ion laser, a semiconductor laser, a Nd:YAG laser, a Ho:YAG laser, etc.

In the composite optical fiber according to the present invention, the large-diameter core of the laser light transmitting portion may be formed of pure quartz glass, with the cladding being formed of fluorine-doped quartz glass. With this design, an excimer laser such as XeCl, KrF or ArF can also be used as a light source.

Laser light emitted from the laser oscillator 10 travels through the optical fiber 41 and enters the laser applying and image observing optical assembly 42, in which it passes through the condenser lens 43b, is reflected by the beam splitter 44 to get into the condenser lens 43a as an incident optical element, where it is processed to become passable through the composite optical fiber 34; thereafter, the laser light travels through the composite optical fiber 34 to be introduced into the objective end 30A, where it is focused by the objective lens unit 23 or 31 to irradiate the lesion.

Illuminating laser light from the illuminator 51 passes through the lightguide fiber 32 to be introduced into the objective end 30A, where it is focused with the surgical laser beam to irradiate the lesion.

The image carrying laser light is reflected from the lesion and travels in opposite direction to pass through the objective end 30A, composite optical fiber 34, condenser lens 43a, beam splitter 44, relay lens subunit 45, interference filter 46, and finally through the camera lens 47 to form a focused image on the CCD camera 48 which outputs an image signal that reaches the video monitor 49 which displays the image of the illuminated lesion on the screen.

The following are typical examples of endoscopic laser therapy that may be practiced by using the endoscopic system of the present invention.

Laser Angioplasty

As a thrombus in an artery is observed, the Nd:YAG laser light is directed at the occlusion to evaporate and cauterize it. Also possible are laser vascular anastomosis and coronary artery bypass surgery.

Crushing Urinary Tract Calculi With Laser

The fiberscope in the endoscopic system of the invention is inserted into the urinary tract and with the position of the stone being checked on the display screen, Ho:YAG laser light or the like is precisely directed at the stone to crush it.

Fundus Photocoagulation

The current practice of fundus photocoagulation involves transmitting argon ion laser light over an optical fiber under endoscopic observation. If the endoscopic system of the present invention is used, the fiberscope needs to be inserted only at one site and yet one can perform coaxial and accurate laser irradiation to perform surgery.

Diagnosis and Treatment Involving Laser Application to Photosensitive Materials

In the treatment of coronary arteriosclerosis or other disease, a material having tumor affinity and photosensitivity, say, a hematoporphyrin derivative (HpD) is administered. Tumor cells in which HpD has accumulated are irradiated with exciting laser light as from an excimer laser of extremely low energy, whereupon HpD emits fluorescence. The resulting fluorescence spectrum peculiar to HpD is detected in the image transmitting section and observed with a CCD camera as a two-dimensional image. Alternatively, the fluorescence spectrum may be connected to a spectroscope and analyzed for diagnostic purposes.

If desired, the laser light source may be switched over to a near infrared laser light source such as Nd:YAG laser and the lesion that has been found to be a tumor by diagnosis is irradiated with the laser light so that it is evaporated and cauterized for treatment.

Similarly, cancer cells may be diagnosed and treated by laser light irradiation using photosensitive materials.

What is claimed is:

1. An endoscopic system, comprising:
    a composite optical fiber consisting essentially of
        a large-diameter, laser light transmitting optical fiber and
        a large number of image transmitting fibers that are bundled together to form an integral assembly with a central fiber,
        the large-diameter optical fiber being surrounded by the image transmitting fibers and
        the image transmitting optical fibers being fused to form a monolithic sea-island structure in which a large number of cores as islands are surrounded by a continuous phase of a cladding as a sea;
    a laser treatment and image observing optical unit that is connected to an eyepiece portion of said composite optical fiber such that the unit launches laser light into said large-diameter optical fiber and such that an image being transmitted through said image transmitting optical fiber is focused on a camera to become observable, and
    an illuminating light transmitting unit that transmits illuminating light to a tip of an objective portion of said composite optical fiber for irradiation purposes, where said illuminating light transmitting unit includes a light source and a light guide that transmits the illuminating light emerging from said light source, at least the tip portion of said light guide being made integral with said image transmitting optical fibers in its longitudinal direction, and
    wherein said large-diameter, laser light transmitting optical fiber and said image transmitting optical fibers are each an optical fiber having a core and of which a core/cladding index difference $\Delta$ is 3.5 to 4%.

2. The endoscopic system according to claim 1, which further includes a video monitor for displaying an image signal as it is picked up from said laser treatment and image observing optical unit.

3. The endoscopic system according to claim 1, wherein said laser treatment and image observing optical unit includes a beam splitter that reflects the emission of laser light from a laser oscillator to be launched into said large-diameter, laser light transmitting optical fiber and which beam splitter transmits the image traveling through said image transmitting optical fiber so that it is focused on said camera.

4. The endoscopic system according to claim 1, wherein the cladding of the large-diameter, laser light transmitting optical fiber is made of a fluorine or otherwise doped quartz glass having a lower reflective index than that of the core of the large-diameter, laser light transmitting optical fiber which is made of pure quartz glass or a $GeO_2$ doped quartz glass, and the cladding of the image transmitting optical fiber is made of pure quartz glass or a fluorine or otherwise doped quartz glass having a lower reflective index than that of the core of the image transmitting optical fiber which is made of a GeO$_2$ doped quartz glass.

5. An endoscopic system according to claim 1, wherein the image transmitting fiber is used for transmitting infrared radiation.

6. An endoscopic system, comprising:
a composite optical fiber consisting essentially of
  a large-diameter, laser light transmitting optical fiber and
  a large number of image transmitting fibers that are bundled together to form an integral assembly with a central fiber,
  the large-diameter optical fiber being surrounded by the image transmitting fibers and
  the image transmitting optical fibers being fused to form a monolithic sea-island structure in which a large number of cores as islands are surrounded by a continuous phase of a cladding as a sea;
a laser treatment and image observing optical unit that is connected to an eyepiece portion of said composite optical fiber such that the unit launches laser light into said large-diameter optical fiber and such that an image being transmitted through said image transmitting optical fiber is focused on a camera to become observable, and
an illuminating light transmitting unit that transmits illuminating light to a tip of an objective portion of said composite optical fiber for irradiation purposes,
wherein said laser treatment and image observing optical unit includes a beam splitter that reflects an emission of laser light from a laser oscillator to be launched into said large-diameter, laser light transmitting optical fiber and that transmits an image traveling through said image transmitting optical fiber so that it is focused on said camera,
said illuminating light transmitting unit includes a light source and a light guide fiber that transmits the illuminating light emerging from said light source, at least a tip portion of said light guide fiber being made integral with said image transmitting optical fibers in its longitudinal direction, and
said light guide fiber is made of a multi-component glass suitable for irradiating a wide range and is provided along the composite optical fiber, and
wherein said large-diameter, laser light transmitting optical fiber and said image transmitting optical fibers are each an optical fiber having a core/cladding index difference $\Delta$ is 3.5 to 4%.

7. An endoscopic system, comprising:
a composite optical fiber consisting essentially of
  a large-diameter, laser light transmitting optical fiber and
  a large number of image transmitting fibers that are bundled together to form an integral assembly with a central fiber,
  the large-diameter optical fiber being surrounded by the image transmitting fibers;
a laser treatment and image observing optical unit that is connected to an eyepiece portion of said composite optical fiber such that the unit launches laser light into said large-diameter optical fiber and such that an image being transmitted through said image transmitting optical fiber is focused on a camera to become observable, and
an illuminating light transmitting unit that transmits illuminating light to a tip of an objective portion of said composite optical fiber for irradiation purposes,
wherein said laser treatment and image observing optical unit includes a beam splitter that reflects an emission of laser light from a laser oscillator to be launched into said large-diameter, laser light transmitting optical fiber and that transmits an image traveling through said image transmitting optical fiber so that it is focused on said camera,
the image transmitting optical fibers are fused to form a monolithic sea-island structure in which a large number of cores as islands are surrounded by a continuous phase of a cladding as a sea,
said illuminating light transmitting unit includes a light source and a light guide fiber that transmits the illuminating light emerging from said light source, at least a tip portion of said light guide fiber being made integral with said image transmitting optical fibers in its longitudinal direction;
said light guide fiber is made of a multi-component glass suitable for irradiating a wide range and is provided along the composite optical fiber, and
wherein said large-diameter, laser light transmitting optical fiber and said image transmitting optical fibers are each an optical fiber having a core/cladding index difference $\Delta$ is 3.5 to 4%.

8. An endoscopic system, comprising:
a composite optical fiber consisting essentially of
  a large-diameter, laser light transmitting optical fiber and
  a large number of image transmitting fibers that are bundled together to form an integral assembly with a central fiber, the large-diameter optical fiber being surrounded by the image transmitting fibers;
a laser treatment and image observing optical unit that is connected to an eyepiece portion of said composite optical fiber such that the unit launches laser light into said large-diameter optical fiber and such that an image being transmitted through said image transmitting optical fiber is focused on a camera to become observable, and
an illuminating light transmitting unit that transmits illuminating light to a tip of an objective portion of said composite optical fiber for irradiation purposes, wherein
the large-diameter, laser light transmitting optical fiber comprises a core made of a GeO$_2$ doped quartz glass and a cladding made a quartz glass, a diameter of the core is in the range of 50 to 400 μm whereas a diameter of the cladding ranges from 1.02 to 1.3 times the core diameter, and the cladding of the large-diameter, laser light transmitting optical fiber has a lower reflective index that that of the core of the optical fiber, a value of a core/cladding difference $\Delta$ being between 3.5 to 4%;
the image transmitting optical fibers are fused to form a monolithic sea-Island structure in which a large number of cores as islands are surrounded by a continuous phase of a cladding as a sea, the cores are made of a GeO$_2$ doped quartz glass, the cladding is made of pure quartz glass or a fluorine doped quartz glass, and a value of a core/cladding index difference $\Delta$ is adjusted between 3.5 to 4%. to reduce a core-to-core spacing to as small as 3 μm; and
the illuminating a light transmitting unit comprises a light source and a light guide fiber which consists of a multi-component glass suitable for irradiating a wide range of area and an angle of viewing of 60 to 120° and is provided along the composite optical fiber.

9. An endoscopic system, comprising:
a composite optical fiber consisting essentially of
  a large-diameter center fiber transmitting laser light, and image transmitting optical fibers surrounding the large-diameter center fiber,
the image transmitting fibers being bundled together to form an integral assembly with the large-diameter center fiber, being fused to form a monolithic sea-island structure in which a large number of cores as islands are surrounded by a continuous phase of cladding as a sea,
a first portion of said image transmitting optical fibers being used for irradiation purposes and
a second portion of said image transmitting optical being used for observing a blood flow;
a laser treatment and image observing optical unit that is connected to an eyepiece portion of said composite optical fiber, to input laser light into said large-diameter center fiber, and to observe an image received through said second portion of the image transmitting optical fibers focused on a camera; and
an illuminating light transmitting unit that transmits illuminating light to a tip of an objective portion of the composite optical fiber for irradiation purposes,
wherein said illuminating light transmitting unit includes a light source and a light guide optical fiber that transmits the illuminating light emerging from said light source to the first portion of said image transmitting optical fibers used for irradiation purposes.

10. The endoscopic system according to claim 9, wherein said large-diameter center fiber and said image transmitting optical fibers are each an optical fiber which has $GeO_2$ doped quartz glass as a core and a core/cladding index difference $\Delta$ is 2 to 5%.

11. The endoscopic system according to claim 9, further including a video monitor for displaying the image received through said second portion of the image transmitting optical fibers.

12. The endoscopic system according to claim 9, wherein said laser treatment and image observing optical unit includes a beam splitter that directs laser light emitted by a laser oscillator into said large-diameter center fiber and transmits the image received through said second portion of image transmitting optical fibers to be focused on said camera.

13. The endoscopic system according to claim 9, wherein a cladding of said large-diameter center fiber is made of a fluorine or otherwise doped quartz glass having a lower reflective index than that of a core of the large-diameter center fiber which is made of pure quartz glass or $GeO_2$ doped quartz glass, and a cladding of the image transmitting optical fibers is made of pure quartz glass or a fluorine or otherwise doped quartz glass having a lower reflective index than that of a core of the image transmitting optical fibers which is made of $GeO_2$ doped quartz glass.

14. The endoscopic system according to claim 9, wherein the image transmitting fibers are used for transmitting infrared radiation.

15. An endoscopic system, comprising:
a composite optical fiber consisting essentially of
a large-diameter center fiber transmitting laser light, and
image transmitting optical fibers surrounding the large-diameter center fiber,
the image transmitting fibers being bundled together to form an integral assembly with the large-diameter center fiber, being fused to form a monolithic sea-island structure in which a large number of cores as islands are surrounded by a continuous phase of cladding as a sea,
a first portion of said image transmitting optical fibers being used for irradiation purposes and
a second portion of said image transmitting optical fibers being used for observing a blood flow;
a laser treatment and image observing optical unit that is connected to an eyepiece portion of said composite optical fiber, to input laser light into said large-diameter center fiber, and to observe an image received through said second portion of the image transmitting optical fibers focused on a camera; and
an illuminating light transmitting unit that transmits illuminating light to a tip of an objective portion of the composite optical fiber,
wherein
said laser treatment and image observing optical unit includes a beam splitter that directs laser light emitted by a laser oscillator into said large-diameter center fiber and transmits the image received through said second portion of image transmitting optical fibers to be focused on said camera,
said illuminating light transmitting unit includes a light source and a light guide optical fiber that transmits the illuminating light emerging from said light source to the first portion of said image transmitting optical fibers used for irradiation purposes, and
said light guide optical fiber is made of a multi-component glass suitable for illuminating a wide range of area and is provided along the composite optical fiber.

16. An endoscopic system, comprising:
a composite optical fiber consisting essentially of
a large-diameter center fiber transmitting laser light, and
image transmitting optical fibers surrounding the large-diameter center fiber,
the image transmitting fibers being bundled together to form an integral assembly with the large-diameter center fiber,
a first portion of said image transmitting optical fibers being used for irradiation purposes and
a second portion of said image transmitting optical fibers being used for observing a blood flow;
a laser treatment and image observing optical unit that is connected to an eyepiece portion of said composite optical fiber, to input laser light into said large-diameter center fiber, and to observe an image received through said second portion of the image transmitting optical fibers focused on a camera; and
an illuminating light transmitting unit that transmits illuminating light to a tip of an objective portion of the composite optical fiber,
wherein
said laser treatment and image observing optical unit includes a beam splitter that directs laser light emitted by a laser oscillator into said large-diameter center fiber and transmits the image received through said second portion of image transmitting optical fibers to be focused on said camera,
said image transmitting optical fibers are fused to form a monolithic sea-island structure in which cores are as islands surrounded by a continuous phase cladding as a sea, and
said illuminating light transmitting unit includes a light source and a light guide optical fiber that transmits the illuminating light emerging from said light source to the first portion of said image transmitting optical fibers, said light guide optical fiber being connected to the first portion of the image transmitting optical fibers used for irradiation purposes, and said light guide optical fiber is made of a multi-component glass suitable for illuminating a wide range and is provided along the composite optical fiber.

17. An endoscopic system, comprising:
a composite optical fiber consisting essentially of
   a large-diameter center fiber transmitting laser light, and
   image transmitting optical fibers surrounding the large-diameter center fiber,
   the image transmitting fibers being bundled together to form an integral assembly with the large-diameter center fiber,
   a first portion of said image transmitting optical fibers being used for irradiation and
   a second portion of said image transmitting optical fibers being used for observing a blood flow;
a laser treatment and image observing optical unit that is connected to an eyepiece portion of said composite optical fiber, to input laser light into said large-diameter center fiber, and to observe an image received through said second portion of the image transmitting optical fibers focused on a camera; and
an illuminating light transmitting unit that transmits illuminating light to a tip of an objective portion of the composite optical fiber, wherein
said large-diameter center fiber has a core made of $GeO_2$ doped quartz glass and a cladding made of quartz glass, a diameter of the core being between 50 and 400 μm and a diameter of the cladding being 1.02 to 1.03 times the diameter of the core, the cladding of the large-diameter center fiber having a reflective index lower than a reflective index of the core of the large-diameter center fiber,
the image transmitting optical fibers are fused to form a monolithic sea-island structure in which cores are as islands surrounded by a continuous phase cladding as a sea, the cores of the image transmitting optical fibers being made of $GeO_2$ doped quartz glass, and the continuous phase cladding being made of pure glass or a fluorine doped quartz glass, which a core/cladding index difference Δ being 2 to 5%, a core-to-core spacing being down to 3 μm, and
said illuminating light transmitting unit includes a light source and a light guide optical fiber which consists of a multi-component glass suitable for illuminating a wide range of area and an angle of viewing of 60 to 120°, said light guide optical fiber being connected to the first portion of the image transmitting optical fibers used for irradiation.

\* \* \* \* \*

UNITED STATES PATENT AND TRADEMARK OFFICE
CERTIFICATE OF CORRECTION

PATENT NO. : 7,582,057 B2
APPLICATION NO. : 11/061722
DATED : September 1, 2009
INVENTOR(S) : Tomoaki Toriya et al.

It is certified that error appears in the above-identified patent and that said Letters Patent is hereby corrected as shown below:

Column 10, Line 48, Claim 8 change "index that" to --index than--.

Column 10, Line 52, Claim 8 change "sea-Island" to --sea-island--.

Column 10, Line 58, Claim 8 change "4%." to --4%--.

Signed and Sealed this

Fifth Day of January, 2010

David J. Kappos
*Director of the United States Patent and Trademark Office*